(12) United States Patent
Börtlein et al.

(10) Patent No.: US 8,986,361 B2
(45) Date of Patent: Mar. 24, 2015

(54) DELIVERY SYSTEM FOR DEPLOYMENT OF MEDICAL DEVICES

(75) Inventors: Georg Börtlein, Meudon (DE); Edward Pannek, El Cajon, CA (US)

(73) Assignee: Medtronic Corevalve, Inc., Minneapolis, MN (US)

( * ) Notice: Subject to any disclaimer, the term of this patent is extended or adjusted under 35 U.S.C. 154(b) by 969 days.

(21) Appl. No.: 12/253,858

(22) Filed: Oct. 17, 2008

(65) Prior Publication Data

US 2010/0100167 A1     Apr. 22, 2010

(51) Int. Cl.
| | |
|---|---|
| A61F 2/06 | (2013.01) |
| A61F 2/95 | (2013.01) |
| A61F 2/24 | (2006.01) |
| A61F 2/97 | (2013.01) |
| A61F 2/966 | (2013.01) |

(52) U.S. Cl.
CPC ............... *A61F 2/95* (2013.01); *A61F 2/2436* (2013.01); *A61F 2/97* (2013.01); *A61F 2002/9665* (2013.01)
USPC ........................................ 623/1.11; 606/198

(58) Field of Classification Search
CPC ..................................................... A61F 2/954
USPC .............. 623/1.11, 2.11, 1.12, 1.23
See application file for complete search history.

(56) References Cited

U.S. PATENT DOCUMENTS

| 3,334,629 A | 8/1967 | Cohn |
|---|---|---|
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |

(Continued)

FOREIGN PATENT DOCUMENTS

| CN | 2007-10007443.3 | 8/2007 |
|---|---|---|
| DE | 3640745 | 6/1987 |

(Continued)

OTHER PUBLICATIONS

U.S. Appl. No. 12/250,163, filed Oct. 13, 2008.

(Continued)

*Primary Examiner* — Katrina Stransky (57) ABSTRACT

A sheathed catheter system is described where the sheath comprises a distal portion and a proximal portion that are moveable axially relative to each other, and relative to a tube carrying a medical device thereon. The distal and proximal sheath portions can be brought together in order to enclose therewithin the medical device. The distal sheath has a proximal section that is configured to bias radially inwardly to minimize an otherwise exposed annular surface catching on protruding surfaces that may exist on the catheter or other medical tool in use at the time, or to minimize scraping the inner native lumen of the patient upon retrieval.

11 Claims, 5 Drawing Sheets

(56) References Cited

U.S. PATENT DOCUMENTS

| | | |
|---|---|---|
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,534,007 A * | 7/1996 | St. Germain et al. ........ 623/1.11 |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,989,280 A * | 11/1999 | Euteneuer et al. ............. 623/1.1 |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |

(56) References Cited

U.S. PATENT DOCUMENTS

| | | |
|---|---|---|
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,416,536 B1 * | 7/2002 | Yee ............................ 623/1.11 |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,947 B1 * | 3/2003 | Euteneuer et al. ............ 623/1.11 |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,645,240 B2 * | 11/2003 | Yee ............................. 623/1.11 |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,004,964 B2 * | 2/2006 | Thompson et al. .......... 623/1.11 |
| 7,018,401 B1 | 3/2006 | Hyodoh et al. |
| 7,022,133 B2 | 4/2006 | Yee et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,320,703 B2 * | 1/2008 | DiMatteo et al. ............ 623/1.12 |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |

(56) References Cited

U.S. PATENT DOCUMENTS

| | | |
|---|---|---|
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163189 A1* | 8/2003 | Thompson et al. .......... 623/1.11 |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0038495 A1* | 2/2005 | Greenan .......... 623/1.11 |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0080474 A1* | 4/2005 | Andreas et al. .......... 623/1.11 |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |

(56) References Cited

U.S. PATENT DOCUMENTS

| | | |
|---|---|---|
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0136036 A1* | 6/2006 | Thompson et al. ......... 623/1.11 |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0038295 A1 | 2/2007 | Case et al. |
| 2007/0043381 A1* | 2/2007 | Furst et al. ................ 606/108 |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233222 A1* | 10/2007 | Roeder et al. .............. 623/1.11 |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0234940 A1 | 9/2010 | Dolan |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A | 7/2000 |
| EP | 0103546 | 3/1984 |
| EP | 0597967 | 12/1994 |
| EP | 0850607 | 7/1998 |
| EP | 1057459 A1 | 6/2000 |

(56) References Cited

FOREIGN PATENT DOCUMENTS

| | | |
|---|---|---|
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| WO | 91/17720 | 11/1991 |
| WO | 93/01768 | 2/1993 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 2009/111241 | 9/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2006/026371 | 3/2006 |
| WO | 2008/047354 | 4/2008 |
| WO | 2008/100599 | 8/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |

OTHER PUBLICATIONS

U.S. Appl. No. 61/192,199, filed Sep. 15, 2008.
U.S. Appl. No. 12/253,858, filed Oct. 17, 2008.
U.S. Appl. No. 12/596,343, filed Apr. 14, 2008.
U.S. Appl. No. 61/129,170, filed Jun. 9, 2008.
Andersen, H.R. et al., "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004; pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

(56) References Cited

OTHER PUBLICATIONS

Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.
Yonga, et al, "Percutaneous Balloon Mitral Valvotomy: Initial Experience in Nairobi Using a New Multi-Track Catheter System," East African Medical Journal (Kenya), Feb. 1999, pp. 71-74.
Yonga, et al, "Percutaneous Transluminal Balloon Valvuloplasty for Pulmonary Valve Stenosis: Report on Six Cases," East African Medical Journal (Kenya), Apr. 1994, pp. 232-235.
Yonga, et al, "Percutaneous Transvenous Mitral Commissurotomy in Juvenile Mitral Stenosis," East African Medical Journal (Kenya), Apr. 2003, pp. 172-174.
Commeau et al, "Percutaneous balloon dilatation of calcific aortic valve stenosis: anatomical and haemodynamic evaluation," 1988, British Heart Journal, 59:227-238.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, *Edwards LifeSciences v. Cook Biotech Inc.*, High Court of Justice—Chancery Division, Patents Court, United Kingdom, Claim No. HC 08CO0934 (83 pages).
Expert report of Dr. Nigel Buller, non-confidential annex—infringement, dated Jan. 12, 2009, *Edwards LifeSciences v. Cook Biotech Inc.*, High Court of Justice—Chancery Division, Patents Court, United Kingdom, Claim No. HC 08CO0934 (12 pages).
Expert report of Dr. Rodolfo Quijano, dated Jan. 9, 2009, *Edwards LifeSciences v. Cook Biotech Inc.*, High Court of Justice—Chancery Division, Patents Court, United Kingdom, Claim No. HC 08CO0934 (18 pages).
First Expert report of Prof. David Williams, dated Jan. 12, 2009, *Edwards LifeSciences v. Cook Biotech Inc.*, High Court of Justice—Chancery Division, Patents Court, United Kingdom, Claim No. HC 08CO0934 (41 pages).
First Expert report of Prof. Martin Rothman, dated Jan. 12, 2009, *Edwards LifeSciences v. Cook Biotech Inc.*, High Court of Justice—Chancery Division, Patents Court, United Kingdom, Claim No. HC 08CO0934 (64 pages).
Fourth Expert report of Prof. Martin Rothman, dated Apr. 22, 2009, *Edwards LifeSciences v. Cook Biotech Inc.*, High Court of Justice—Chancery Division, Patents Court, United Kingdom, Claim No. HC 08CO0934 (10 pages).
Second Expert report of Dr. Nigel Buller, dated Feb. 25, 2009, *Edwards LifeSciences v. Cook Biotech Inc.*, High Court of Justice—Chancery Division, Patents Court, United Kingdom, Claim No. HC 08CO0934 (24 pages).
Second Expert report of Dr. Rodolfo Quijano, dated Feb. 26, 2009, *Edwards LifeSciences v. Cook Biotech Inc.*, High Court of Justice—Chancery Division, Patents Court, United Kingdom, Claim No. HC 08CO0934 (6 pages).
Second Expert report of Prof. David Williams, dated Feb. 5, 2009, *Edwards LifeSciences v. Cook Biotech Inc.*, High Court of Justice—Chancery Division, Patents Court, United Kingdom, Claim No. HC 08CO0934 (15 pages).
Second Expert report of Prof. Martin Rothman, dated Feb. 5, 2009, *Edwards LifeSciences v. Cook Biotech Inc.*, High Court of Justice—Chancery Division, Patents Court, United Kingdom, Claim No. HC 08CO0934 (11 pages).
Third Expert report of Dr. Nigel Buller, dated Apr. 21, 2009, *Edwards LifeSciences v. Cook Biotech Inc.*, High Court of Justice—Chancery Division, Patents Court, United Kingdom, Claim No. HC 08CO0934 (6 pages).
Third Expert report of Dr. Rudolfo Quijano, dated Apr. 27, 2009, *Edwards LifeSciences v. Cook Biotech Inc.*, High Court of Justice—Chancery Division, Patents Court, United Kingdom, Claim No. HC 08CO0934 (3 pages).
Third Expert report of Prof. David Williams, dated Apr. 22, 2009, *Edwards LifeSciences v. Cook Biotech Inc.*, High Court of Justice—Chancery Division, Patents Court, United Kingdom, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R. Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.

(56) References Cited

OTHER PUBLICATIONS

First Expert report of Dr. Anthony C. Lunn (7 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

First Witness statement of Stanton Rowe (9 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

Second Witness statement of Stanton Rowe (3 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

First Expert report of Professor Martin Terry Rothman (75 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

Reply Expert report of Professor Martin Terry Rothman (9 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

First Expert report of Richard A. Hillstead (41 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

Reply Expert report of Richard A. Hillstead (9 pages), *Corevalve, Inc. v. Edwards Lifesciences AG and Edwards Lifesciences PVT, Inc.,* High Court of Justice—Chancery Division Patents Court, United Kingdom, Case No. HC-07-C01243.

Expert Rebuttal Report of Prof. Martin T. Rothman (32 pages) redacted, *Edwards v. CoreValve,* U.S. District Court, District of Delaware, Case No. 08-091, dated Jul. 29, 2009.

Expert Report of Prof. Martin T. Rothman (74 pages) redacted, *Edwards v. CoreValve,* U.S. District Court, District of Delaware, Case No. 08-091, dated Jun. 29, 2009.

\* cited by examiner

DELIVERY SYSTEM FOR DEPLOYMENT OF MEDICAL DEVICES

BACKGROUND OF THE INVENTION

1. Field of the Invention

The present invention relates generally to an apparatus and method for deploying a medical device from a minimally invasive delivery system, such as a delivery catheter, and deploying the device within a patient.

2. Description of the Related Art

Percutaneous aortic valve replacement (PAVR) technology is emerging that provides an extremely effective and safe alternative to therapies for aortic stenosis specifically, and aortic disease generally. Historically, aortic valve replacement necessitated open heart surgery with its attendant risks and costs. The replacement of a deficient cardiac valve performed surgically requires first placing the patient under full anesthesia, opening the thorax, placing the patient under extracorporeal circulation or peripheral aorto-venous heart assistance, temporarily stopping the heart, exposing and excising the deficient valve, and then implanting a prosthetic valve in its place. This procedure has the disadvantage of requiring prolonged patient hospitalization, as well as extensive and often painful recovery. Although safe and effective, surgical aortic valve replacement (SAVR) presents advanced complexities and significant costs. For some patients, however, surgery is not an option for one or many possible reasons. As such, a large percentage of patients suffering from aortic disease go untreated.

To address the risks associated with open-heart implantation, devices and methods for replacing a cardiac valve by less invasive means have been developed. For example, CoreValve, Inc. of Irvine, Calif. has developed a prosthetic valve fixed to a collapsible and expandable support frame that can be loaded into a delivery catheter. Such a bioprosthesis may be deployed in-situ minimally invasively through the vasculature at significantly less patient risk and trauma. A description of the CoreValve bioprosthesis and various embodiments appears in U.S. Pat. Nos. 7,018,406 and 7,329,278, and published Application Nos. 2004/0210304 and 2007/0043435. By using a minimally invasive replacement cardiac valve, patient recovery is greatly accelerated over surgical techniques. In the case of the CoreValve device, the support frame is made from shape memory material such as Nitinol. Other catheter-delivery valve replacement systems use stainless steel, or do not rely upon a rigid frame.

As demonstrated successfully to date, using a transcatheter procedure, percutaneous aortic valve replacement proceeds by delivering a prosthetic valve to the diseased valve site for deployment, either using a balloon to expand the valve support against the native lumen or exposing a self-expanding support in situ and allowing it to expand into place. With the latter, the self-expanding frame remains sheathed during delivery until the target site is reached. Advantageously, the frame may be secured to the catheter to avoid premature deployment as the sheath is withdrawn. In the CoreValve valve prosthesis, a hub is employed with two lateral buttons or ears around each of which a loop or alternatively a frame zig may reside during delivery. The internal radial force of the sheath keeps the frame compressed against the catheter, including the frame zigs in place around the lateral buttons. The catheter generally comprises at least two tubes, an inner tube that carries the prosthesis and a central tube that carries the sheath, permitting the sheath to move relative to the prosthesis.

As with traditional cardiovascular interventional therapies, transcatheter device deployment may proceed retrograde against normal blood flow, or antegrade, with blood flow. For percutaneous aortic valve replacement, entry through the femoral arteries proceeds in a retrograde format up through the iliac, the descending aorta, over the arch and to the native annulus. In some cases, entry has been made closer to the arch; for example through the left subclavian artery. Antegrade procedures have been performed where delivery takes place through the venous system transseptally to the native aortic annulus. More recently, transapical procedures have been performed whereby a cardiac surgeon delivers a catheter through the patient's chest wall, then through the exposed left ventricle apex and then to the target site.

With retrograde deployment, it is generally desired that the catheter be advanced within the vasculature so that the device is positioned where desired at the annulus site. With some embodiments under development, the desired site is the annulus itself With the CoreValve device, the desired site extends from the annulus to the ascending aorta, given its relative length. In the transfemoral approach, when the CoreValve device is positioned at the desired site, the sheath is withdrawn to the point where the inflow end of the device (preferably positioned at the native annulus) expands to engage and push radially outwardly the native valve leaflets. The sheath continues to be withdrawn proximally as the prosthesis continues to expand as it is exposed until the sheath covers just the outflow portion of the prosthesis still secured to the hub ears. Any readjustment of the axial position of the device in situ can be made during this process based upon electronic visual feedback during the procedure. Once well positioned, the sheath is fully withdrawn, the device fully expands in place, and the catheter is withdrawn through the center of the device and out through the vasculature. While it would be possible to deploy the prosthetic device such that the sheath could be withdrawn distally so that the outflow end of the prosthesis deploys first, such an arrangement would require advancing distally the central tube of the catheter connected to the sheath distally. In the case of transfemoral retrograde delivery, that would cause the central tube to project well into the left ventricle, which is not desirable. In a antegrade approach, for example transapical delivery, the reverse situation exists. There it is more desirable to advance the sheath distally to expose the inflow end of the prosthesis at the native annulus first. The native anatomy can accommodate this distal deployment because the central tube carrying the sheath is advanced up the ascending aorta towards the arch. Like the retrograde approach, once the valve prosthesis is fully deployed, the catheter may be withdrawn through the center of the prosthesis and removed through the apex of the heart.

Regardless of the direction of approach, with self-expanding frame technology, it is sometimes observed that even well-placed prosthetic valves inadvertently shift from the intended target site a small distance during the final delivery stage. The valve may still function effectively, but it is not optimized when, for example, the valve is placed so that it projects more than desired into the left ventricle. If the frame is implanted too low into the left ventricle, there is a risk of paravalvular leak where a portion of the blood ejected from the ventricle returns through the frame below the annulus.

In doing so, the catheter may sometimes inadvertently advance into the left ventricle for one of several possible reasons. One theory is that conical expansion of the zigs of the frame may influence positioning by following the path of least resistance until the inflow section is completely deployed in both the annulus and the ascending aorta may cause the prosthesis to shift. Another is the friction between the catheter sheath and the vessel wall, which may limit retraction of sheath even though the operator is pulling on it through the handle button. Consequently, the valve is pushed distally through the forward action of the plunger rather than the valve remaining stationary relative to the target site by the retraction of the sheath in the proximal direction. If the valve is not fully deployed (i.e., the sheath is not fully retracted) so that the valve frame is still secured to the catheter, axial adjustment is still possible. This is known as dynamic catheter positioning. In some cases, however, it is not determined until after full deployment that the frame is deployed amiss. In that circumstance, a repositioning procedure might need to be taken to correct placement. While possible in one of several different ways, it adds a level of complexity to the medical procedure that would be preferably avoided if possible. The problem is exacerbated because with transcatheter delivery, unlike surgical implantation, the clinician is unable to directly see the target site and must rely upon videographic technology to assess appropriate placement of the prosthesis.

One solution is to split the sheath into two discrete sections; a proximal section and a distal section. Doing so permits a controlled deployment that is central to the device, rather than at the distal or proximal end as with a single sheath. In U.S. Pat. No. 7,238,197, Seguin et al. have suggested such an arrangement, without any specificity or demonstration. See col. 14:36-42. No mention is made of the benefits or advantages of doing so, nor the particular configuration. Another example is shown in U.S. Pat. No. 7,022,133 to Yee et al. However, the distal and proximal portions are overlapping. Moreover, that disclosure does not address the issue regarding minimizing inaccurate deployment once the prosthesis is positioned at the target site. With an ill-configured split sheath arrangement, it has been observed that withdrawal of the catheter post-deployment may cause the proximal portion of the distal sheath to cause trauma to the native lumen where the vasculature is arcuate, such as the aortic arch. The problem may be encountered regardless of whether delivery proceeds antegrade or retrograde.

It is therefore desired to provide a transluminal catheter that enables prosthesis implantation accurately at the target location without the need for dynamic catheter positioning upon sheath retrieval. It is expected that, with such a solution, the prosthesis implantation procedure would become easier to manage with the desirable result that final positioning becomes more consistent.

SUMMARY OF THE INVENTION

The invention described and claimed herein comprises embodiments for minimally invasively delivering a medical device to a patient. The apparatus comprises a sheathed catheter system comprising an inner tube and a central tube, wherein the central tube has an outside surface suitable for accepting a medical device collapsed thereon in a stationary fashion. The sheath comprises a distal portion and a proximal portion that are moveable axially relative to each other, and with respect to the central tube, and can be brought together to abut in order to enclose therewithin a bioprosthesis such as a self-expanding frame supporting a tissue valve. In one embodiment, the distal sheath has a proximal section that is configured to bias radially inwardly to minimize a larger exposed annular surface that may catch on protruding surfaces or may scrape the native lumen surface of the patient upon retrieval. In another embodiment, a retaining hub for retaining a portion of the medical device being delivered comprises an extended portion that is generally cylindrical, or may have a non-tapered surface, such that it is configured to maintain low profile engagement with the distal sheath portion. Such an arrangement can also, when the distal sheath is retrieved, minimize vascular trauma or avoid being impeded by irregular surfaces. As contemplated, there are several different embodiments that can be made to employ the invention claimed herein. These and other features, aspects and advantages of embodiments of the present invention are described in greater detail below in connection with drawings of the apparatus and method, which is intended to illustrate, but not to limit, the embodiments of the present invention.

Thus one embodiment of the invention provides an apparatus for minimally invasively delivering a medical device to a target site within a patient, the apparatus comprising a first tube having an outside surface suitable for accepting a medical device collapsed thereon in a stationary position; and a sheath comprising first and second portions that may be moved axially relative to each other and with respect to the first tube, the sheath portions configured so as to enclose a medical device collapsed onto the first tube when brought together, and configured to expose the medical device when directed away from each other, the first sheath portion comprising a section that is normally biased radially inwardly so as to maintain a low profile.

Another embodiment of the invention provides an apparatus for delivering a medical device to a target site within a patient via a body lumen, the apparatus comprising: an inner tube; a distal sheath portion attached to the inner tube; an intermediate tube, moveable over the inner tube and at least partially into the distal sheath portion; an outer tube, moveable over the intermediate tube; a proximal sheath portion attached to the outer tube, so that, in use, the proximal sheath portion and the distal sheath portion can be moved together to substantially cover a medical device mounted on the intermediate tube and moved apart to deploy the medical device; the distal sheath portion having a proximal end portion configured to extend away from the walls of the body lumen when, in use, the sheath portions are apart and the distal sheath portion is moved proximately.

Another embodiment of the invention provides an apparatus for minimally invasively delivering a medical device to a target site within a patient, the apparatus comprising: a first tube having an outside surface suitable for accepting a medical device collapsed thereon in a stationary position, the first tube comprising a hub for retaining at least a portion of a medical device on the first tube, wherein the hub comprises a generally extended non-tapered portion; and a sheath comprising first and second portions that may be moved axially relative to each other and with respect to the first tube, the sheath portions configured so as to enclose a medical device collapsed onto the first tube when brought together, and configured to expose the medical device when directed away from each other; wherein, during operation, the first sheath portion may be moved in a direction sufficient to expose the medical device while said first sheath portion still covers at least a part of the extended non-tapered portion of the hub.

Yet another embodiment of the invention provides an apparatus for delivering a medical device to a target site within a patient via a body lumen, the apparatus comprising: an inner tube; a distal sheath portion attached to the inner tube; an intermediate tube, moveable over the inner tube and at least partially into the distal sheath portion, the intermediate tube having a hub at its distal end and having a region on the intermediate tube proximal of the hub for mounting the medical device; an outer tube, moveable over the intermediate tube; a proximal sheath portion attached to the outer tube, so that, in use, the proximal sheath portion and the distal sheath portion can be moved together to substantially cover a medical device mounted on the intermediate tube and moved apart to deploy the medical device; the hub having an axial length sufficient to permit the medical device to be deployed while the distal sheath portion covers at least part of the hub.

DETAILED DESCRIPTION OF THE PREFERRED EMBODIMENT

Figure 1A:
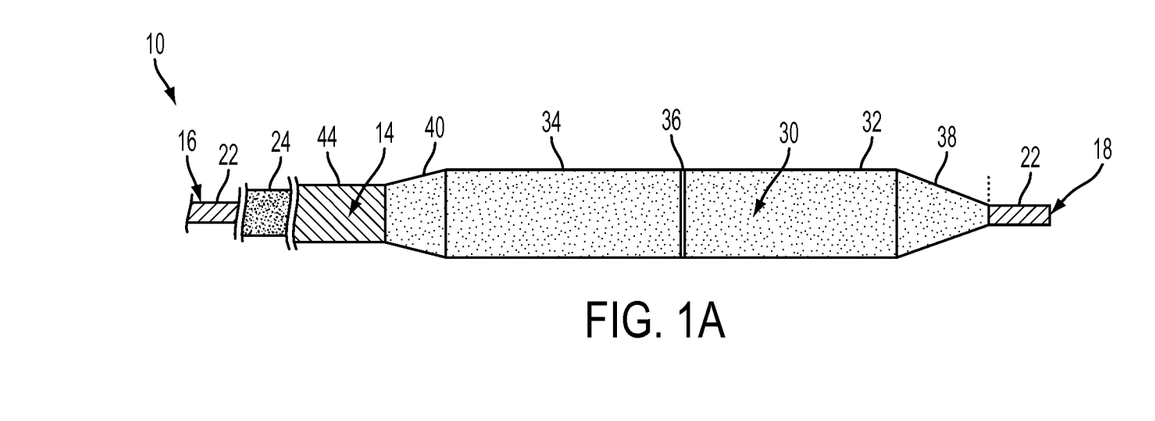
FIGS. 1A and 1B show schematic views of a catheter having a sheath with distal and proximal portions.
Figure 1B:
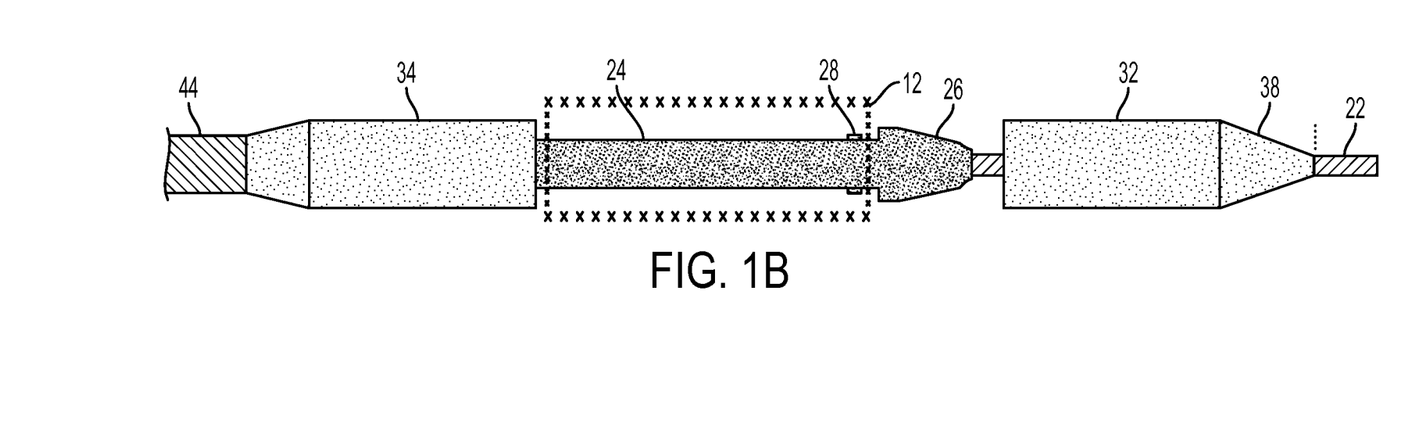

Referring to FIGS. 1A and 1B, an example of a split sheath delivery system embodiment 10 for delivering a medical device 12 comprises a catheter 14 having a proximal end 16 and a distal end 18. In the figures shown, and by way of example, the medical device 12 is a self-expanding frame.

The split sheath catheter 14 of FIGS. 1A and 1B comprises a first inner tube 22 and a central tube 24, all of which may be controlled by the clinician. At the distal end of the central tube 24 is a hub or cap 26 affixed to the central tube 24. The hub 26 is preferably tapered distally and configured to have a smooth rounded surface at its distal-most end. The hub is further configured to comprise at least one but preferably two or more buttons 28 for assisting in retaining the medical device 12 until full deployment. Depending upon the configuration and arrangement, as well as semantics, the buttons may be described as projecting ears, tabs, or hooks. It is important to note that a hub is not required for the invention described herein.

The catheter 14 further comprises a sheath 30 preferably made of resilient pliable material, such as those used in the industry. The sheath may comprise in whole or in part a braided, woven, or stitched structure, a polymer, or may comprise an inflatable balloon. The sheath 30 comprises a distal portion 32 and a proximal portion 34 that when pulled together to form joint 36 fully enclose the medical device 12 within. A first end 38 of distal sheath portion 32 is affixed to the central surface of inner tube 22 proximal its distal end 18. The proximal sheath portion 34 is affixed at its proximal end 40 to an exterior tube 44 that extends in the proximal direction and covers both the proximal portions of central tube 24 and inner tube 22 in a preferably concentric configuration.

Figure 2A:
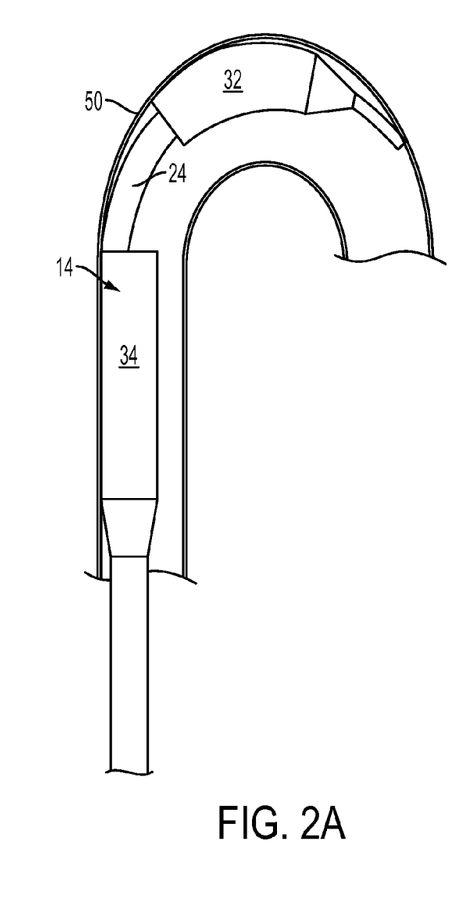
FIGS. 2A and 2B show schematic views of the catheter of FIGS. 1A and 1B inserted within the vasculature.
Figure 2B:
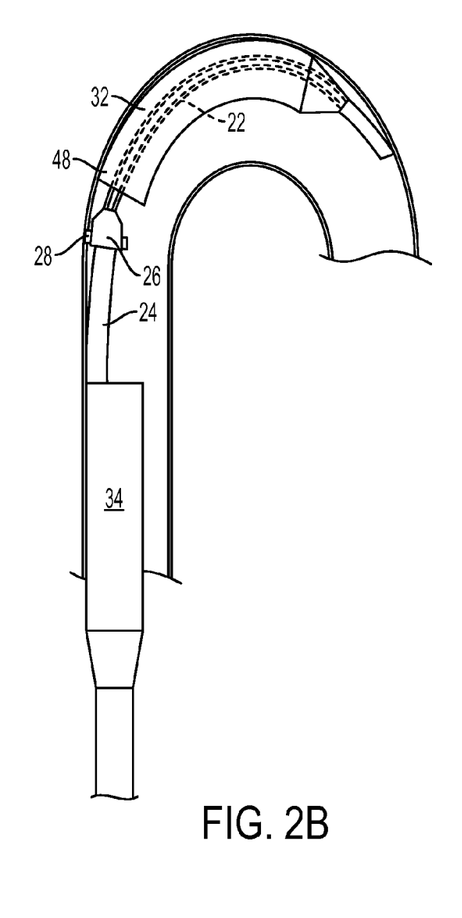

As shown in FIG. 1A, when the distal and proximal portions 32, 34 of sheath 30 are adjoined at joint 36, the medical device 12 is covered, thus permitting delivery of the medical device 12 to the desired target site. As shown in FIG. 1B, when the distal and proximal portions 32, 34 of sheath 30 are directed away from each other, the medical device 12 is exposed and permitted to expand. Referring to FIGS. 2A and 2B, one limitation with a split sheath arrangement may be appreciated. FIG. 2A shows a split sheath catheter embodiment similar to the one illustrated in FIGS. 1A-B and inserted within a patient's vasculature; in particular, the aortic arch 50 (with peripheral vessels not shown). When the distal and proximal sheath portions 32, 34 are directed apart, the central tube 24 carrying the medical device (not shown) is exposed so that the medical device may be released. Upon retrieval of the distal sheath 32, however, given the curvilinear nature of the native vasculature, the proximal end 48 of distal sheath 32 is pressed tightly up against the endothelial lining of the native lumen. Movement of the proximal end 48 in a proximal direction may cause trauma to the vasculature. Moreover, in a split sheath catheter embodiment where a hub 26 is employed or where the hub has buttons 28 that extend radially outward, the proximal end 48 of distal sheath 32 may also catch on the buttons 28 as the distal sheath is moved proximally.

In an effort to avoid these issues, another embodiment of split sheath catheter, shown in FIGS. 3A through 3G, comprises a distal sheath having an inwardly biased proximal section. Specifically, alternative split sheath delivery embodiment 110 for delivering a medical device 112 comprises a catheter 114 that comprises an inner tube 122 (with an optional internal lumen for passing a guide wire therethrough) where the inner tube 122 is concentrically positioned within a central tube 124. In the embodiment illustrated, the medical device 112 can be a self-expanding frame supporting a valve such as CoreValve's aortic valve prosthesis.

At the distal tip of the central tube 124 is a hub 126 having a generally tapered distal configuration and at least one but preferably two or more buttons 128 (FIG. 3D) for retaining the medical device 112 during travel. Enclosing the central tube 124, hub 126 and medical device 112 is split sheath 130 comprising a distal sheath portion 132 and proximal sheath portion 134 that are configured to abut together at joint 136 to fully enclose the medical device 112 therewithin. The distal sheath portion 132 comprises a tapered section 138 affixed to the distal end of inner tube 122. The proximal sheath portion 134 comprises a proximally tapered section 140 that forms external tube 144 controllable by the clinician. It should be noted that the relative size of the distal sheath 132 to the proximal sheath 134 is not critical, so it may be a ratio of 50/50 or a ratio where one is larger than the other.

When it is desired to expose the medical device 112, the distal sheath portion 132 is directed in the distal direction 160 while the proximal sheath portion 134 is directed in the proximal direction 170. In preferably stepped deployment fashion, the distal and proximal sheath portions 132, 134 are directed moved away from each other to the point that each portion still retains the respective distal end 112A and proximal end 112B of the medical device 112. The sequence of movement is not critical; i.e., it is not critical whether the proximal sheath is directed proximally before or after the distal sheath is directed distally. The distal sheath portion 132 is moved distally by directing the inner tube 122 distally 160, while the proximal sheath portion 134 may be moved proximally by pulling the external tube 144 in the proximal direction 170. By stepped deployment, more accurate placement of the medical device at the target site may be permitted. When the mid-portion of the medical device 112 expands to engage the luminal surface of the vasculature, the clinician can assess whether it is placed in situ at the desired location. If not, the catheter system 114 may be moved into either distally or proximally as needed.

Figure 3A:
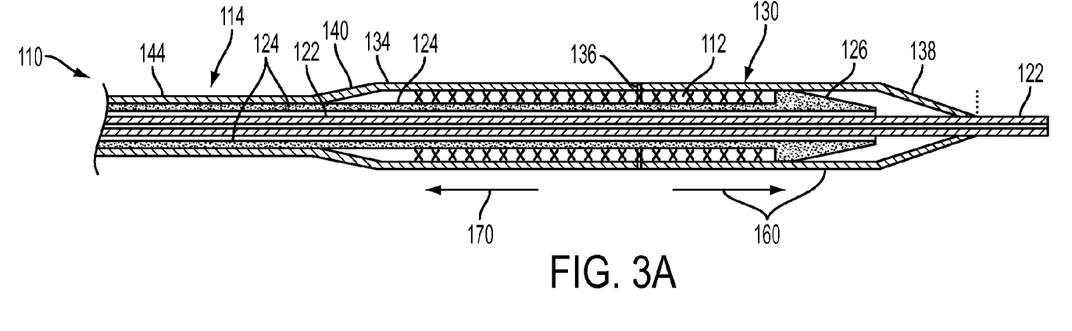
FIGS. 3A-E show cross-sectional views of one embodiment of a device delivery system showing sequential axial movement of proximal and distal sheath portions.
Figure 3B:
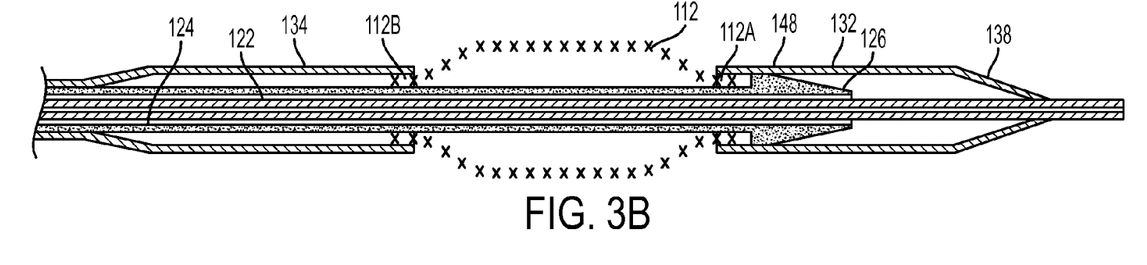
Figure 3C:
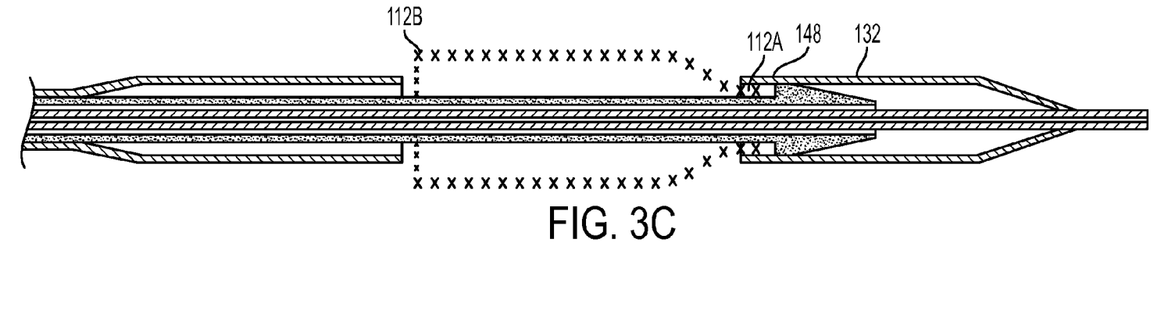
Figure 3D:
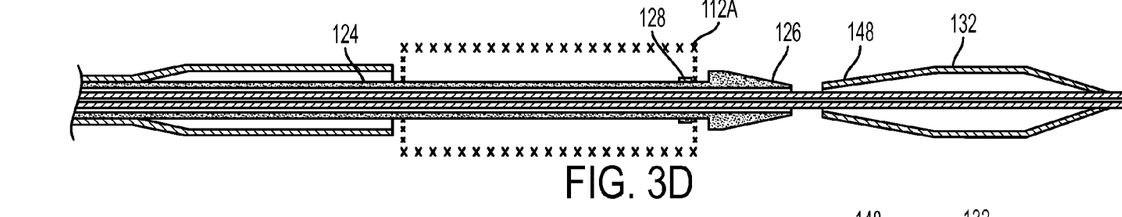

When it is determined that the medical device 112 is properly positioned, the proximal sheath portion 134 may be further moved proximally to expose the proximal end 112B of the medical device and permit expansion thereof, as shown in FIG. 3C. With the medical device 112 more firmly positioned in the vasculature, the distal sheath portion 132 may be advanced further distally to release the distal end 112A of the medical device. The medical device is now fully deployed, as shown in FIG. 3D. Preferably, the distal sheath portion 132 has a proximal section 148 that is configured to radially bias inwardly when unconstrained. By continuing to advance the distal sheath portion 132 in the distal direction 160 beyond the axial position of the hub 126, the proximal section 148 of the distal sheath portion 132 collapses inwardly toward the inner tube 122. This reduces the profile of the distal sheath portion 132. The proximal section 148 of distal sheath 132 may be made of a membrane (e.g., polyurethane, silicon, etc.) elastically expandable up to a given diameter to host the prosthesis, or a generally cylindrical layer that can fold back along predetermined pleats to a smaller profile (e.g., ePTFE, Dacron™, etc.) so that its natural state is to be collapsed. Preformed polymeric material, encapsulated spring material or the like, are contemplated. Alternatively, it could be made with longitudinal splits inside a conventional sheath that tend to fold back towards the inner side when a given radial force (of the folded prosthesis) is removed; or it could be made by expansion of elastic material. Other materials and/or other modes of preparing the sheath 130 for effective function are also contemplated to achieve the functions described herein.

Figure 3E:
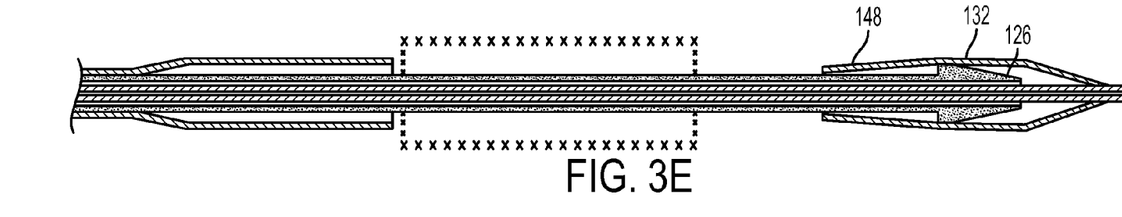
Figure 3F:
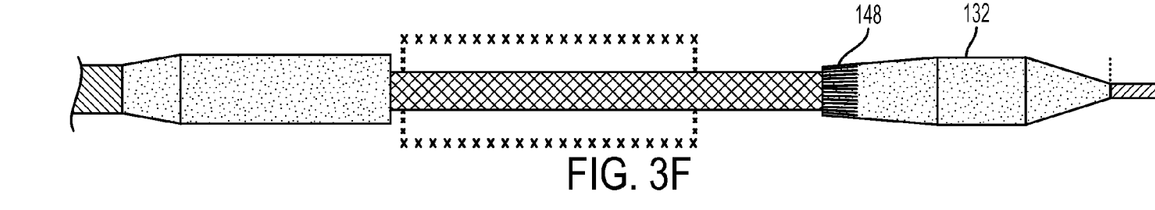
FIGS. 3F and 3G show schematic views of the delivery system of FIGS. 3A-E.
Figure 3G:
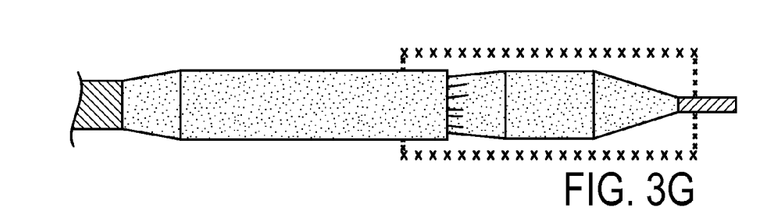

By either withdrawing the inner tube 122 with distal sheath portion 132 proximally, or by advancing the central tube 124 and hub 126 distally (as shown in FIGS. 3E and 3F), the distal sheath portion 132 may enclose the hub 126. The resilient nature of the proximal section 148 permits it to be expanded so as to permit the hub 126 to advance within the distal sheath portion 132. With this arrangement, a smoother and lower profile is created for withdrawing the catheter through the medical device 112 in the proximal direction 170, as shown in FIG. 3F.

Figure 4A:
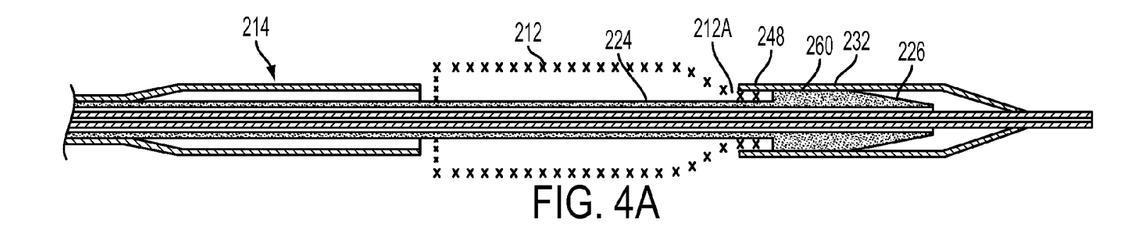
FIGS. 4A-D show cross-sectional and schematic views of a second embodiment of a device delivery system showing sequential axial movement of distal sheath relative to an internal tube.
Figure 4B:
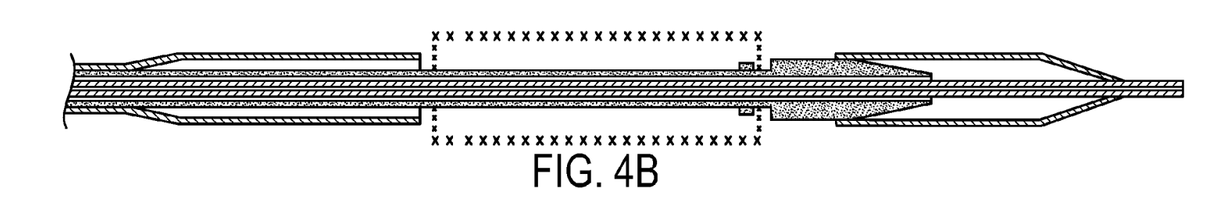
Figure 4C:
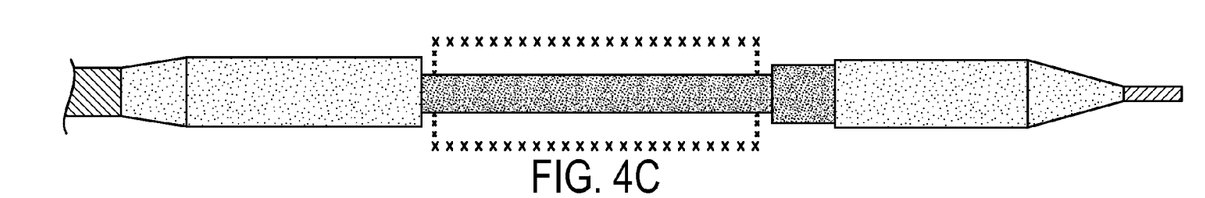
Figure 4D:
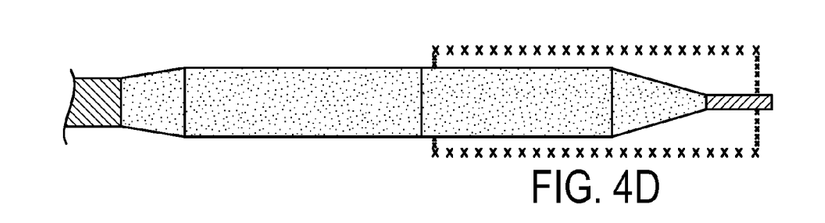

Referring to FIGS. 4A-4D, an alternative embodiment catheter 214 comprises similar components as described above, including a central tube 224 with hub 226 at a distal end thereof. The catheter system 214 further comprises a distal sheath portion 232 having a proximal section 248 enclosing the distal end 212A of medical device 212. When being delivered to the target site, the distal sheath portion 232 encloses the hub 226. After proper placement of the medical device 212 in situ, the medical device may be fully deployed, as shown in FIG. 4B, by advancing the distal sheath portion 232 distally to expose the distal end 212A of the medical device. In this embodiment, it is contemplated that the hub 226 have an elongate configuration with an extended cylindrical portion 260 that results in a hub 226 longer than the hubs 26 and 126 of other embodiments described herein. With this configuration, the distally-advanced distal sheath portion 232 need not advance beyond the distal end of hub 226 (see FIGS. 4B and 4C). The distal sheath portion 232 may maintain a low profile by remaining biased against the hub 226 for retrieval through the deployed medical device 212. This may also be advantageous where it is preferred not to advance any portion of the catheter too far past the target site, for example, circuitous vasculature like the aortic arch. As shown in FIG. 4D, the catheter 214 may be withdrawn proximally through the deployed medical device 212.

It should be understood that the terms distal and proximal as used herein are with reference to the clinician and that other inventive embodiments contemplated may orient the catheters 14, 114 and 214 differently with respect to the vasculature, depending upon the entry point and the target site. It is also contemplated that either the distal sheath portion or proximal sheath portion, or both, could be configured so as to invert outwardly or inwardly, as described further in co-pending and co-owned application Ser. No. 12/212,620 filed on Sep. 17, 2008. By way of example, instead of the distal sheath portion 132 of FIG. 3C being moved distally with the inner tube 122 to expose the distal end 112A of medical device 112, the distal sheath portion could be inverted at a distal position and drawn into the interior of inner tube 122.

In operation, the catheters described are particularly suited for delivery of a heart valve, where precise placement is important. Other critical and less-critical target sites are also contemplated. In the case of a self-expanding aortic valve replacement, the catheter may be delivered transfemorally, transeptally, transapically or through the sub-clavian, among other possible entry ways. In one procedure, the catheter is deployed so that the valved frame is positioned entirely aligned with the target site; e.g., aortic annulus up to ascending aorta. The frame may then be exposed from one end to the other, depending upon the direction of delivery, by either advancing the inner tube relative to the central tube or vice versa, or retraction of the central shaft. As the frame is exposed, it expands outwardly to engage the native intimal lining so placement accuracy is maximized. When the sheath is fully removed and the frame fully expanded, the catheter may then be withdrawn though the functioning prosthetic valve and removed from the patient.

Although embodiments of this invention have been disclosed in the context of certain preferred embodiments and examples, it will be understood by those skilled in the art that the embodiments of the present invention extend beyond the specifically disclosed embodiments to other alternative embodiments and/or uses of the invention and obvious modifications and equivalents thereof. In particular, while the present loading system and method has been described in the context of particularly preferred embodiments, the skilled artisan will appreciate, in view of the disclosure, that certain advantages, features, and aspects of the system may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. An apparatus for minimally invasively delivering a medical device to a target site within a patient, the apparatus comprising:
a first tube having an outside surface suitable for accepting the medical device collapsed thereon in a stationary position; and
a sheath including first and second portions that may be moved axially relative to each other and with respect to the first tube, the sheath portions configured so as to enclose the medical device collapsed onto the first tube when brought together, and configured to expose the medical device when directed away from each other, the first sheath portion including a proximal edge,
wherein the proximal edge is elastically expandable from a first diameter to a second diameter, and
wherein the proximal edge is biased radially inwardly to the first diameter when unconstrained such that the first sheath portion tapers proximally toward the first tube to reduce a profile thereof, and
wherein the proximal edge is held at the second diameter by the medical device collapsed onto the first tube.

2. The apparatus of claim 1, wherein the first tube includes a hub.

3. The apparatus of claim 2, wherein the first sheath portion is configured so as to enclose at least a portion of the hub.

4. The apparatus of claim 1, wherein either the first and/or second sheath portion is configured to invert upon itself.

5. An apparatus for minimally invasively delivering a medical device to a target site within a patient, the apparatus comprising:
   a first tube having an outside surface suitable for accepting the medical device collapsed thereon in a stationary position, the first tube including a hub for retaining at least a portion of the medical device on the first tube,
   wherein the hub includes a generally extended non-tapered portion, and
   wherein the hub includes at least one button configured to retain the medical device on the hub until full deployment of the medical device; and
   a sheath including first and second portions that may be moved axially relative to each other and with respect to the first tube, the sheath portions configured so as to enclose the medical device collapsed onto the first tube when brought together, and configured to expose the medical device when directed away from each other,
   wherein the first sheath portion includes an elastically expandable proximal edge that is biased radially inwardly against the medical device collapsed onto the first tube when the sheath portions enclose the medical device, and
   wherein, during operation, when the first sheath portion is moved in a direction sufficient to expose the medical device the elastically expandable proximal edge is biased radially inwardly against the extended non-tapered portion of the hub and tapers proximally toward the first tube to maintain a low profile.

6. An apparatus for delivering a medical device to a target site within a patient via a body lumen, the apparatus comprising:
   an inner tube;
   a distal sheath portion attached to the inner tube;
   an intermediate tube, moveable over the inner tube and at least partially into the distal sheath portion;
   an outer tube, moveable over the intermediate tube;
   a proximal sheath portion attached to the outer tube, so that, in use, the proximal sheath portion and the distal sheath portion can be moved together to substantially cover the medical device mounted on the intermediate tube and moved apart to deploy the medical device;
   the distal sheath portion having an elastic proximal edge biased radially inwardly to a first diameter when unconstrained such that the distal sheath portion tapers proximally toward the inner tube to reduce a profile thereof and the distal sheath portion being configured to expand from the first diameter to a second diameter to cover the medical device.

7. The apparatus for delivering a medical device of claim 6, wherein the proximal edge is tapered inwardly.

8. The apparatus for delivering a medical device of claim 6, wherein the proximal edge is pleated.

9. The apparatus for delivering a medical device of claim 6, wherein the proximal edge is beveled.

10. An apparatus for delivering a medical device to a target site within a patient via a body lumen, the apparatus comprising:
    an inner tube;
    a distal sheath portion attached to the inner tube,
    wherein the distal sheath portion includes an elastic proximal edge biased radially inwardly to a first diameter when unconstrained such that the distal sheath portion tapers proximally toward the inner tube to reduce a profile thereof and the elastic proximal edge being expandable from the first diameter to a second diameter to cover the medical device;
    an intermediate tube, moveable over the inner tube and at least partially into the distal sheath portion, the intermediate tube having a hub at its distal end and having a region on the intermediate tube proximal of the hub for mounting the medical device,
    wherein the region for mounting the medical device includes at least one button configured to retain the medical device on the hub until full deployment of the medical device;
    an outer tube, moveable over the intermediate tube; and
    a proximal sheath portion attached to the outer tube, so that, in use, the proximal sheath portion and the distal sheath portion can be moved together to substantially cover the medical device mounted on the intermediate tube and moved apart to deploy the medical device;
    the hub having an axial length sufficient to permit the medical device to be deployed while the distal sheath portion covers at least part of the hub.

11. The apparatus for delivering a medical device of claim 10, wherein the hub comprises a substantially cylindrical outer surface over which the distal sheath portion can reside until the medical device is deployed.

* * * * *